(12) United States Patent
Huang et al.

(10) Patent No.: US 9,714,202 B2
(45) Date of Patent: Jul. 25, 2017

(54) METHOD FOR PRODUCING ADAMANTANE

(71) Applicant: CPC CORPORATION, TAIWAN, Taipei (TW)

(72) Inventors: Ming-Yu Huang, Chiayi (TW); Jann-Chen Lin, Chiayi (TW); Yih-Ping Wang, Chiayi (TW); Jung-Chung Wu, Chiayi (TW)

(73) Assignee: CPC Corporation, Taiwan, Taipei (TW)

(*) Notice: Subject to any disclaimer, the term of this patent is extended or adjusted under 35 U.S.C. 154(b) by 200 days.

(21) Appl. No.: 14/546,667

(22) Filed: Nov. 18, 2014

(65) Prior Publication Data

US 2015/0344385 A1    Dec. 3, 2015

(30) Foreign Application Priority Data

Jun. 3, 2014    (TW) .............. 103119239 A

(51) Int. Cl.
| | | |
|---|---|---|
| *C07C 5/29* | (2006.01) | |
| *B01J 31/08* | (2006.01) | |
| *B01J 31/02* | (2006.01) | |

(52) U.S. Cl.
CPC ............ *C07C 5/29* (2013.01); *B01J 31/0202* (2013.01); *B01J 31/0209* (2013.01); *B01J 31/08* (2013.01); *B01J 2231/52* (2013.01); *C07C 2103/74* (2013.01); *C07C 2527/126* (2013.01); *C07C 2531/02* (2013.01); *C07C 2531/04* (2013.01); *C07C 2531/26* (2013.01)

(58) Field of Classification Search
CPC   C07C 5/29; C07C 13/615; B01J 31/08; B01J 31/0202; B01J 31/0209
See application file for complete search history.

(56) References Cited

U.S. PATENT DOCUMENTS

| | | | | |
|---|---|---|---|---|
| 3,274,274 A | * | 9/1966 | Cupery ................. | C07C 17/10 585/352 |
| 3,457,317 A | * | 7/1969 | Trottier ................. | C07C 5/29 585/352 |
| 3,944,626 A | | 3/1976 | Honna et al. | |
| 7,488,859 B2 | | 2/2009 | Huang et al. | |
| 8,017,821 B2 | * | 9/2011 | Huang ................. | B01J 31/0278 585/363 |
| 2001/0051755 A1 | | 12/2001 | Kawai et al. | |
| 2003/0018226 A1 | | 1/2003 | Kojima et al. | |

FOREIGN PATENT DOCUMENTS

| | | |
|---|---|---|
| CN | 1340483 A | 3/2002 |
| CN | 1935756 A | 3/2007 |
| CN | 101125791 A | 2/2008 |
| CN | 101407442 A | 4/2009 |

OTHER PUBLICATIONS

Schleyer, "A Simple Preparation of Adamantane", J. Am. Chem. Soc., (1957), 3292, 79.
Olah et al., "Chemistry in Superacids. 6 Perfluoroalkanesulfonic Acid-Boron Perfluoroalkanesulfonates: New Superacid Systems for Generation of Carbocations and Catalysts for Electrophilic Transformations of Hydrocarbons", J. Org. Chem., (1984), 4591-4594, 49.
Dzurilla et al., "Synthesis, properties, and reactions of heterodienes. II. Reactions of cinnamoyl isothiocyanates with enamines and spectral study of the reaction products", Chem. zvesti, (1973), 488-496, 27 (4).

\* cited by examiner

*Primary Examiner* — In Suk Bullock
*Assistant Examiner* — Jason Chong
(74) *Attorney, Agent, or Firm* — The Webb Law Firm

(57) ABSTRACT

A method for producing adamantane includes the steps of preparing a catalytic composition including an acidic ionic liquid and a co-catalyst and subjecting a tetrahydrodicyclopentadiene-containing component to isomerization in the presence of the catalytic composition to form adamantane. The acidic ionic liquid includes aluminum chloride and a quaternary onium compound selected from the group consisting of a quaternary ammonium halide, a quaternary phosphonium halide, and a combination thereof. The co-catalyst is an oxygen-containing reagent.

9 Claims, No Drawings

METHOD FOR PRODUCING ADAMANTANE

CROSS-REFERENCE TO RELATED APPLICATION

This application claims priority from Taiwanese Application No. 103119239, filed on Jun. 3, 2014, the entire disclosure of which is hereby incorporated by reference.

FIELD OF THE INVENTION

The invention relates to a method for producing adamantane, more particularly to a method for producing adamantane using a catalytic composition including an acidic ionic liquid and a co-catalyst.

BACKGROUND OF THE INVENTION

Adamantane (tricyclo[3,3,1,1$^{3,7}$]decane, $C_{10}H_{16}$) is a colorless, non-toxic, crystalline compound having a structure of highly symmetrically cyclic tetrahedron. The chemical and physical properties of adamantane are as follows: melting point of 268° C., good heat stability and lubricity, ease of sublimation, good solubility in an organic solvent, and poor solubility in water.

Since hydrogen atoms in adamantane are easily substituted, adamantane can be converted into various derivatives thereof through a reaction such as bromination, oxidation, or alkylation. As adamantane and derivatives thereof may be used to produce fragrances, persistent pesticides, dyes, medicines, etc., they have wide potential use in the fields of medicine, textile, functional polymers, lubricants, surfactants, catalysts, photosensitive materials, etc. However, high manufacturing costs limit the application and development of adamantane.

In general, adamantane is produced via isomerization of tetrahydrodicyclopentadiene (referred to as THDCPD hereinafter and including exo-THDCPD and endo-THDCPD). THDCPD is produced via catalytic hydrogenation of dicyclopentadiene (a petroleum by-product, referred to as DCPD hereinafter, and including endo-DCPD and exo-DCPD), and most of the THDCPD produced in this manner is endo-THDCPD.

The scheme for producing adamantane is shown below:

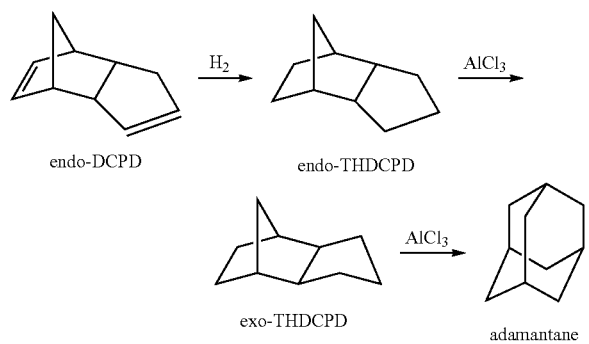

Conventional methods for producing adamantane via isomerization of THDCPD include an aluminum (III) chloride method, a solid acid method, a superacid method, and an acidic ionic liquid method.

The aluminum (III) chloride method is performed by dissolving endo-THDCPD in a solvent and subjecting endo-THDCPD to isomerization directly using a solid catalyst of $AlCl_3$ under proper reaction conditions to form adamantane. The yield of adamantane is about 15-20% (see, for example, Schleyer, *J. Am. Chem. Soc.*, (1957), 79, 3292). There are various modifications of the aluminum (III) chloride method. For example, CN 101407442A discloses addition of a co-catalyst, such as sodium carbonate and sodium chloride, to the catalyst of $AlCl_3$, and CN 1340483A discloses addition of a co-catalyst, such as alcohol, ether, ester, acid, and $C_2$-$C_{10}$ alkyl halide, to the catalyst of $AlCl_3$. Although the yield of adamantane is larger than 50% in CN 101407442A and CN 1340483A, there are the following disadvantages: (1) a large amount of tar may be produced so that a complicated refining process is required to purify the resultant adamantane; (2) a large amount of the catalyst of $AlCl_3$ is required and recycling of $AlCl_3$ is difficult as $AlCl_3$ is dispersed in the whole reaction system after the isomerization; and (3) separation of $AlCl_3$ from the resultant adamantane requires use of an alkaline liquid followed by washing with a large amount of water, which produces a considerable amount of waste, resulting in environmental problems.

CN 101125791A discloses a solid catalyst system in which $AlCl_3$ is supported on a molecular sieve. Although a liquid product may be easily separated from the solid catalyst system, the solid catalyst system need to be used under high hydrogen pressure (for example, 2.5 MPa) and at elevated temperature (for example, 160° C.)., and the yield of adamantane is relatively low (for example, a 30% yield).

The solid acid method is proposed to solve the problems that the $AlCl_3$ catalyst cannot be reused and a considerable amount of waste catalyst need to be further treated. Solid acid catalysts have been industrially used by Idemitsu Petrochemical Co., Ltd. to produce adamantane. In U.S. Pat. No. 3,944,626 and US 20030018226 owned by Idemitsu, there is disclosed use of a solid acid catalyst, in which a metal selected from Pt, Re, Co, Ni, Fe, Cu, Ge, and the like is supported on zeolite by means of an ion exchange method, for isomerizing THDCPD at a temperature of 250□ and under a hydrogen pressure of 1-3 MPa to form adamantane along with a ring-opened product (an isomer of $C_{10}H_{18}$), and the yield of adamantane is up to about 30%. Additionally, CN 1935756 discloses an adamantane synthesizing method wherein a full-silicon medium-hole molecular sieve solid acid, which is surface-treated by an inorganic acid, is used as a catalyst for producing adamantane at a temperature of 250° C. under a hydrogen pressure of 1 Mpa. Although the solid acid catalyst may be reused, the synthesizing method needs to be performed at an elevated temperature and under a high hydrogen pressure, and a large amount of by-products may be produced.

In the superacid method, a superacid catalyst is used for isomerizing THDCPD into adamantane. Adamantane may be advantageously obtained when the acidity of the superacid catalyst is enhanced. US 20010051755 discloses a process for producing adamantane in which a HF—$BF_3$ catalyst added with a co-catalyst such as platinum/activated carbon is used. When the process is performed at a temperature of 50° C. and under a hydrogen pressure of 1.5 MPa, the conversion rate of THDCPD is above 78%, and the selectivity of adamantane is above 88%. Additionally, it is disclosed in Synthesis, (1973), 488 and *J. Org. Chem.* (1984), 49, 4591 that THDCPD is isomerized at a temperature of 100° C. using a superacid catalyst of B $(OSO_2CF_3)_3$—$HSO_3CF_3$ to produce adamantane at a yield of 47-64%. Although superacid catalysts has high activity and high selectivity so that the superacid method for producing adamantane has a better effect, they are highly corrosive. Furthermore, the technologies related to mass production of superacid catalysts and to equipment for producing adamantane using superacid catalysts are still immature, and thus the superacid method is unsuitable for industrial use.

The recently developed acidic ionic liquid method is disclosed in, for example, U.S. Pat. No. 7,488,859. An acidic ionic liquid has many advantages. For example, it is usually not miscible with adamantane so that recycling thereof and purification of adamantane become easier. In addition, the pH value of the acidic ionic liquid can be adjusted by modifying the proportions of the components contained therein. When the acidic ionic liquid is used as a catalyst for producing adamantane, there are advantages of high selectivity, easy operation, facile separation from adamantane, etc. However, the conversion rate for the isomerization of THDCPD is relatively low, and thus the yield of adamantane is unsatisfactory.

SUMMARY OF THE INVENTION

Therefore, an object of the present invention is to provide a method for producing adamantane so as to overcome the above-mentioned drawbacks of the acidic ionic liquid method.

According to an aspect of this invention, there is provided a method for producing adamantane, comprising the steps of:

preparing a catalytic composition including an acidic ionic liquid and a co-catalyst, wherein the acidic ionic liquid includes aluminum chloride and a quaternary onium compound selected from the group consisting of a quaternary ammonium halide, a quaternary phosphonium halide, and a combination thereof, and wherein the co-catalyst is an oxygen-containing reagent; and subjecting a tetrahydrodicyclopentadiene-containing component to isomerization in the presence of the catalytic composition to form adamantane.

DETAILED DESCRIPTION OF THE EMBODIMENTS

A method for producing adamantane according to this invention comprises the steps of:

preparing a catalytic composition including an acidic ionic liquid and a co-catalyst, wherein the acidic ionic liquid includes aluminum chloride and a quaternary onium compound selected from the group consisting of a quaternary ammonium halide, a quaternary phosphonium halide, and a combination thereof, and wherein the co-catalyst is an oxygen-containing reagent; and subjecting a tetrahydrodicyclopentadiene-containing component to isomerization in the presence of the catalytic composition to form adamantane.

The quaternary ammonium halide may be any quaternary ammonium halide capable of being mixed with aluminum chloride to form an acidic ionic liquid. Preferably, the quaternary ammonium halide is selected from ammonium halide, pyridinium halide, imidazolium halide, pyrrolium halide, pyridinium halide, pyrimidinium halide, pyrazinium halide, pyridazinium halide, and combinations thereof, or selected from alkyl-substituted type compounds which includes tetraalkylammonium halide, tialkylpyridinium halide, trialkylimidazolium halide, trialkylpyrrolidinium halide, trialkylpiperidinium halide, trialkylpyrimidinium halide, trialkylpyrazinium halide, trialkylpyridazinium halide, and combinations thereof. Each of the alkyl-substituted-type compounds contains an alkyl group having a carbon number ranging from 1 to 18. The quaternary ammonium halide used in the following illustrated examples is selected from pyridine hydrochloride (referred to as PHC hereinafter), 1-butyl-3-methylimidazolium chloride (referred to as BMIC hereinafter), 1-butyl-3-methylimidazolium bromide (referred to as BMIB hereinafter), and tetraethylammonium chloride (referred to as TEAC hereinafter).

The quaternary phosphonium halide may be any quaternary phosphonium halide capable of being mixed with aluminum chloride to form an acidic ionic liquid. Preferably, the quaternary phosphonium halide is tetraalkylphosphonium halide.

Halo anion contained in the quaternary ammonium halide and the quaternary phosphonium halide is selected from $F^-$, $Cl^-$, $Br^-$, and $I^-$.

The aluminum chloride contained in the acidic ionic liquid is in a molar ratio such that the acidic ionic liquid is provided with sufficient acidity. Specifically, the aluminum chloride contained in the acidic ionic liquid is in a molar ratio ranging preferably from 0.5 to 0.9, more preferably from 0.55 to 0.85, and most preferably from 0.6 to 0.75.

Preferably, the oxygen-containing reagent useful as the co-catalyst is selected from the group consisting of water, alcohol, acid, ester, aqueous hydrogen peroxide, aqueous hydrogen chloride, and combinations thereof. A weight ratio of the co-catalyst to aluminum chloride is generally greater than 0.001.

If the co-catalyst is added in an insufficient amount, the catalytic activity of the acidic ionic liquid and thus the yield of adamantane may not be effectively enhanced. On the other hand, if the co-catalyst is added in an excess amount, the catalytic activity of the acidic ionic liquid and thus the yield of adamantane may be reduced. Therefore, when the co-catalyst is selected from water, alcohol, acid, and ester, the molar ratio of the co-catalyst to aluminum chloride ranges preferably from 0.01 to 0.9 and more preferably from 0.02 to 0.5. When the co-catalyst is selected from hydrogen peroxide and hydrogen chloride in the form of an aqueous solution, the weight ratio of the co-catalyst to aluminum chloride ranges preferably from 0.01 to 0.5 and more preferably from 0.02 to 0.2.

The alcohol useful as the co-catalyst may be any mono-alcohol and/or polyol capable of enhancing the catalytic activity of the acidic ionic liquid. When the alcohol is a mono-alcohol, it is preferably a $C_1$-$C_6$ saturated mono-alcohol. When the alcohol is a polyol, it is preferably a $C_2$-$C_6$ saturated polyol, and is more preferably a $C_2$-$C_6$ saturated diol or a $C_3$-$C_6$ saturated triol.

The acid useful as the co-catalyst may be any acid capable of enhancing the catalytic activity of the acidic ionic liquid. Preferably, the acid is a $C_1$-$C_7$ saturated mono-acid.

The ester useful as the co-catalyst may be any ester capable of enhancing the catalytic activity of the acidic ionic liquid. Preferably, the ester is a $C_2$-$C_{13}$ saturated ester.

When aqueous hydrogen peroxide is used as the co-catalyst, it may be used in a concentration capable of enhancing the catalytic activity of the acidic ionic liquid. Preferably, the concentration of the aqueous hydrogen peroxide ranges from 1 to 50 wt %.

When aqueous hydrogen chloride is used as the co-catalyst, it may be used in a concentration capable of enhancing the catalytic activity of the acidic ionic liquid. Preferably, the concentration of hydrogen chloride ranges from 1 to 50 wt %.

The tetrahydrodicyclopentadiene-containing component includes tetrahydrodicyclopentadiene (THDCPD), which may be exo-THDCPD, endo-THDCPD, or a combination thereof. Exo-THDCPD is obtained via isomerization of endo-THDCPD, which is obtained via hydrogenation of endo-DCPD. When endo-THDCPD is obtained in a controlled reaction condition, a small amount of exo-THDCPD may be obtained as well. When exo-THDCPD is obtained in a controlled reaction condition, a small amount of endo-THDCPD may be obtained as well.

When endo-THDCPD is used, the tetrahydrodicyclopentadiene-containing component further includes a solvent for dissolving endo-THDCPD since endo-THDCPD is in solid format room temperature. On the other hand, when exo-THDCPD is used, no solvent is required and exo-THDCPD may be directly subjected to isomerization for producing adamantane since exo-THDCPD is in liquid format room temperature. When the solvent is included in the tetrahydrodicyclopentadiene-containing component, it is used in an amount greater than 0 wt % and up to 50 wt % based on 100 wt % of the tetrahydrodicyclopentadiene-containing component.

The solvent included in the tetrahydrodicyclopentadiene-containing component may be any solvent which is capable of dissolving endo-THDCPD. Preferably, the solvent is selected from $C_5$-$C_{18}$ n-alkanes, $C_5$-$C_{18}$ iso-alkanes, $C_5$-$C_{18}$ neo-alkanes, $C_5$-$C_{18}$ cycloalkanes, $C_1$-$C_5$ halogen-containing hydrocarbons, and combinations thereof. More preferably, the solvent is selected from cyclohexane, exo-THDCPD, and a combination thereof. In the following examples, the solvent is exo-THDCPD.

The isomerization of the tetrahydrodicyclopentadiene-containing component into adamantane is conducted at a temperature ranging preferably from 25 to 150° C., more preferably from 40 to 100° C., further more preferably from 50 to 90° C., and most preferably at 90° C. When the isomerization is conducted at a temperature less than 25° C., the isomerization may not be conducted easily. On the other hand, when the isomerization is conducted at a temperature higher than 150° C., a relatively large amount of by-products may be produced and thus the selectivity of adamantane may be reduced.

EXAMPLES

The following examples are provided to illustrate the embodiments of the invention, and should not be construed as limiting the scope of the invention.

Chemicals:

1. PHC, BMIC, BMIB, TEAC, acetic acid, and glycerol: manufactured by Fluka. Anhydrous PHC was obtained using a drying treatment by exposing PHC in a glove box having a water content of less than 0.5 ppm for 3 days; and 2. $AlCl_3$, DCPD, n-heptane, cyclohexane, ethanol, isopropanol, ethylene glycol, ethyl acetate, 35% $H_2O_{2(aq)}$, 1N $HCl_{(aq)}$, and 37% $HCl_{(aq)}$: manufactured by Merck.

Preparation Example 1

Preparation of Acidic Ionic Liquid

Anhydrous PHC (2.023 g, 0.0175 mole) and $AlCl_3$ (4.334 g, 0.0325 mole) were mixed by stirring at room temperature to form an acidic ionic liquid. The molar ratio of $AlCl_3$ in the acidic ionic liquid is 0.65.

Preparation Example 2

Preparation of endo-THDCPD

A mixture of endo-DCPD and n-heptane in a volume ratio of 1:1 was brought into contact with a Ni-0104T catalyst manufactured by Engelhard at a temperature of 100° C. and at a liquid hourly space velocity (LHSV) of 1 to conduct fixed bed catalytic hydrogenation to obtain endo-THDCPD (yield of almost 100%), followed by removal of n-heptane via distillation to obtain crystalline endo-THDCPD.

Preparation Example 3

Preparation of exo-THDCPD

The acidic ionic liquid prepared in Preparation Example 1 was placed in an oil-bath at a temperature of 70° C. A mixture of endo-THDCPD (6 g) and cyclohexane in a weight ratio of 1:1 was added to the acidic ionic liquid using a syringe, followed by conducting an isomerization reaction at a stirring rate of 400 rpm for 1 hour to obtain exo-THDCPD (yield of 96.7%). Cyclohexane was removed via distillation to obtain a product of exo-THDCPD (purity: >98.4%).

Preparation Example 4

Preparation of a combination of endo-THDCPD and exo-THDCPD

The crystalline endo-THDCPD (6.4 g) prepared in Preparation Example 2 was dissolved in the exo-THDCPD liquid (3.6 g) prepared in Preparation Example 3 to obtain a combination of endo-THDCPD and exo-THDCPD. The ratios of endo-THDCPD and exo-THDCPD in the combination were 65% and 35%, respectively.

Example 1

Preparation of Adamantane

Deionized water, which was used as a co-catalyst (0.084 g, 0.0047 mole), was added to the acidic ionic liquid prepared in Preparation Example 1 in a molar ratio of deionized water to $AlCl_3$ of 0.144 to form a catalytic composition. The combination of endo-THDCPD and exo-THDCPD prepared in Preparation Example 4 (5.963 g, 0.0438 mole) was added to the catalytic composition, followed by an isomerization reaction conducted at 70° C. with stirring at 500 rpm for 5 hours to form a liquid product which is immiscible with and lies above the acidic ionic liquid. White particles were formed in the liquid product when the liquid product was cooled. Cyclohexane (12 g) was added to the liquid product with stirring to dissolve the white particles so as to form an organic liquid layer lying above the acidic ionic liquid.

Analysis of the Composition of the Organic Liquid Layer

The organic liquid layer was taken out using a syringe and was then analyzed for the composition thereof using a gas chromatograph (HP6890, manufactured by Hewlett-Packard) with a wall coated open tubular and non-polar fused silica column manufactured by Chrompack. The operating conditions for the analysis were as follows. Injection volume was 0.2 μl. The analysis temperature was kept at 50° C. for 25 minutes, was then increased at a rate of 5° C./minute to 160 t, was subsequently increased at a rate of 10° C./minute to 280 t, and was kept at 280° C.' for 10 minutes. The detector was a flame ionization detector (FID). The detecting temperature was 270° C.

On the basis of the data obtained from the gas chromatograph, the isomerization conversion, the selectivity, and the yield were determined according to following formulas, respectively.

Isomerization conversion of THDCPD (%)=[1−(the total amount of THDCPD after the isomerization)/(the total amount of THDCPD before the isomerization);

Selectivity of adamantane (%)={(the amount of adamantane)/[(the total amount of THDCPD before the isomerization)−(the total amount of THDCPD after the isomerization)]}×100(%); and Yield of adamantane=[isomerization conversion of THDCPD (%)×selectivity of adamantane (%)]× 100(%), wherein the total amount of THDCPD refers to the total amount of endo-THDCPD and exo-THDCPD.

Example 2

Example 1 was repeated except that deionized water was replaced with ethanol (0.214 g, 0.0047 mole) and the molar ratio of ethanol to $AlCl_3$ was 0.144.

Example 3

Example 1 was repeated except that deionized water was replaced with isopropanol (0.279 g, 0.0047 mole) and the molar ratio of isopropanol to $AlCl_3$ was 0.144.

Example 4

Example 1 was repeated except that deionized water was replaced with ethylene glycol (0.288 g, 0.0047 mole) and the molar ratio of ethylene glycol to $AlCl_3$ was 0.144.

Example 5

Example 1 was repeated except that deionized water was replaced with glycerol (0.428 g, 0.0047 mole) and the molar ratio of glycerol to $AlCl_3$ was 0.144.

Example 6

Example 1 was repeated except that deionized water was replaced with acetic acid (0.279 g, 0.0047 mole) and the molar ratio of acetic acid to $AlCl_3$ was 0.144.

Example 7

Example 1 was repeated except that deionized water was replaced with ethyl acetate (0.410 g, 0.0047 mole) and the molar ratio of ethyl acetate to $AlCl_3$ was 0.144.

Example 8

Example 1 was repeated except that deionized water was replaced with an aqueous $H_2O_2$ solution (35%, 0.187 g) and the weight ratio of the aqueous $H_2O_2$ solution to $AlCl_3$ was 0.043.

Example 9

Example 1 was repeated except that deionized water was replaced with an aqueous HCl solution (1N, 0.186 g) and the weight ratio of the aqueous HCl solution to $AlCl_3$ was 0.043.

Example 10

Example 1 was repeated except that deionized water was replaced with an aqueous HCl solution (37%, 0.184 g) and the weight ratio of the aqueous HCl solution to $AlCl_3$ was 0.043.

Example 11

Example 1 was repeated except that deionized water was used in an amount of 0.13 g (0.0072 mole) and the molar ratio of deionized water to $AlCl_3$ was 0.222.

Example 12

Example 1 was repeated except that deionized water was used in an amount of 0.186 g (0.0103 mole) and the molar ratio of deionized water to $AlCl_3$ was 0.318.

Example 13

Example 1 was repeated except that the isomerization was conducted at 90° C.

Example 14

Example 1 was repeated except that the molar ratio of $AlCl_3$ in the acidic ionic liquid is 0.75, i.e., the acidic ionic liquid used in this example was prepared by mixing anhydrous PHC (1.455 g, 0.0126 mole) with $AlCl_3$ (4.334 g, 0.0378 mole). In addition, deionized water was used in an amount of 0.151 g (0.0084 mole) and the molar ratio of deionized water to $AlCl_3$ was 0.222.

Example 15

Example 1 was repeated except that PHC contained in the acidic ionic liquid was replaced with BMIC (3.057 g, 0.0175 mole).

Example 16

Example 1 was repeated except that PHC contained in the acidic ionic liquid was replaced with BMIB (3.83 g, 0.0175 mole).

Example 17

Example 1 was repeated except that PHC contained in the acidic ionic liquid was replaced with TEAC (2.41 g, 0.0175 mole).

Example 18

Example 1 was repeated except that the combination of endo-THDCPD and exo-THDCPD was replaced with the exo-THDCPD liquid product prepared in Preparation Example 3.

Example 19

Example 18 was repeated except that deionized water was replaced with an aqueous HCl solution (1N, 0.186 g) and the weight ratio of the aqueous HCl solution to $AlCl_3$ was 0.043.

Example 20

Example 18 was repeated except that deionized water was replaced with an aqueous HCl solution (37%, 0.184 g) and the weight ratio of the aqueous HCl solution to AlCl$_3$ was 0.043.

Comparative Example 1

Example 1 was repeated except that the co-catalyst was not added.

Comparative Example 2

Example 18 was repeated except that the co-catalyst was not added.

The reaction conditions, the isomerization conversion of THDCPD, the selectivity of adamantane, and the yield of adamantane in Examples 1-20 and Comparative Examples 1-2 were summed up in Table 1 below.

TABLE 1

| | | | Reaction Conditions: | | | | | Results: | | |
|---|---|---|---|---|---|---|---|---|---|---|
| | | | | Acidic ionic liquid | | | Molar (or weight) ratio of | Isomerization Conversion of | | |
| | | Reactant | Temp. (°C.) | Halide | Molar ratio of AlCl$_3$ | Co-catalyst | co-catalyst to AlCl$_3$ | THDCPD (%) | Selectivity (%) | Yield (%) |
| Ex. | 1 | endo-/exo-THDCPD | 70 | PHC | 0.65 | Deionized water | 0.144** | 24.2 | 72.2 | 17.5 |
| | 2 | endo-/exo-THDCPD | 70 | PHC | 0.65 | Ethanol | 0.144** | 22.1 | 60.1 | 13.3 |
| | 3 | endo-/exo-THDCPD | 70 | PHC | 0.65 | Iso-propanol | 0.144** | 25.5 | 66.6 | 17.0 |
| | 4 | endo-/exo-THDCPD | 70 | PHC | 0.65 | Ethylene glycol | 0.144** | 24.1 | 73.0 | 17.6 |
| | 5 | endo-/exo-THDCPD | 70 | PHC | 0.65 | Glycerol | 0.144** | 27.5 | 69.6 | 19.1 |
| | 6 | endo-/exo-THDCPD | 70 | PHC | 0.65 | Acetic acid | 0.144** | 25.2 | 68.7 | 17.3 |
| | 7 | endo-/exo-THDCPD | 70 | PHC | 0.65 | Ethyl acetate | 0.144** | 27.1 | 55.4 | 15.0 |
| | 8 | endo-/exo-THDCPD | 70 | PHC | 0.65 | 35% H$_2$O$_{2(aq)}$ | 0.043* | 17.5 | 70.5 | 12.3 |
| | 9 | endo-/exo-THDCPD | 70 | PHC | 0.65 | 1N HCl$_{(aq)}$ | 0.043* | 31.2 | 75.2 | 23.5 |
| | 10 | endo-/exo-THDCPD | 70 | PHC | 0.65 | 37% HCl$_{(aq)}$ | 0.043* | 32.0 | 77.5 | 24.8 |
| | 11 | endo-/exo-THDCPD | 70 | PHC | 0.65 | Deionized water | 0.222** | 34.1 | 70.4 | 24.0 |
| | 12 | endo-/exo-THDCPD | 70 | PHC | 0.65 | Deionized water | 0.318** | 31.2 | 75.2 | 23.4 |
| | 13 | endo-/exo-THDCPD | 90 | PHC | 0.65 | Deionized water | 0.144** | 40.8 | 78.2 | 31.9 |
| | 14 | endo-/exo-THDCPD | 70 | PHC | 0.75 | Deionized water | 0.222** | 55.7 | 79.1 | 44.1 |
| | 15 | endo-/exo-THDCPD | 70 | BMIC | 0.65 | Deionized water | 0.144** | 18.7 | 59.6 | 11.1 |
| | 16 | endo-/exo-THDCPD | 70 | BMIB | 0.65 | Deionized water | 0.144** | 17.2 | 63.2 | 10.9 |
| | 17 | endo-/exo-THDCPD | 70 | TEAC | 0.65 | Deionized water | 0.144** | 26.0 | 72.4 | 18.8 |
| | 18 | exo-THDCPD | 70 | PHC | 0.65 | Deionized water | 0.144** | 33.5 | 72.0 | 24.1 |
| | 19 | exo-THDCPD | 70 | PHC | 0.65 | 1N HCl$_{(aq)}$ | 0.043* | 32.7 | 69.1 | 22.6 |
| | 20 | exo-THDCPD | 70 | PHC | 0.65 | 37% HCl$_{(aq)}$ | 0.043* | 35.6 | 72.4 | 25.8 |
| Comp. Ex. | 1 | endo-/exo-THDCPD | 70 | PHC | 0.65 | None | — | 3.1 | 100.0 | 3.1 |
| | 2 | exo-THDCPD | 70 | PHC | 0.65 | None | — | 9.2 | 64.5 | 5.9 |

**the molar ratio of co-catalyst to AlCl$_3$
*the weight ratio of co-catalyst to AlCl$_3$ As shown in Table 1, in Examples 1-10 and Comparative Example 1, the same combination of 65% endo-THDCPD and 35% exo-THDCPD was used, and isomerization was conducted at the same temperature using the same acidic ionic liquid in the same amount. In Comparative Example 1, in which no co-catalyst was used, the yield of adamantane was only 3.1% after isomerization for 5 hours. In Examples 1-7, in which the co-catalyst (i.e., deionized water, ethanol, iso-propanol, ethylene glycol, glycerol, acetic acid, or ethyl acetate) was used in a molar ratio of the co-catalyst to $AlCl_3$ of 1.44, the isomerization conversion of THDCPD was significantly increased, and thus the yield of adamantane was increased (12.3%-24.8%) even though the selectivity of adamantane was slightly reduced. Similarly, in Examples 8-10, in which 35% $H_2O_{2(aq)}$, 1N $HCl_{(aq)}$, or 37% $HCl_{(aq)}$ was used as the co-catalyst in a weight ratio of the co-catalyst to $AlCl_3$ of 0.043, the isomerization conversion of THDCPD was significantly increased, and thus the yield of adamantane was increased as well.

In Examples 18-20 and Comparative Example 2, the same exo-THDCPD (purity >98.4%) was used, and isomerization was conducted at the same temperature using the same acidic ionic liquid in the same amount. In Comparative Example 2, in which no co-catalyst was used, the yield of adamantane was only 5.9%. In Examples 18-20, in which the co-catalyst (i.e., deionized water, 1N $HCl_{(aq)}$, or 37% $HCl_{(aq)}$) was used, the yield of adamantane was increased (22.6%-25.8%).

Regarding the amount of the co-catalyst, as shown in Examples 1, 11, and 12, in which isomerization was conducted at the same temperature using the same acidic ionic liquid in the same amount, when the molar ratio of deionized water to $AlCl_3$ was increased from 0.144 to 0.222, the yield of adamantane was increased from 17.5% to 24.0%. However, when the molar ratio of deionized water to $AlCl_3$ was further increased to 0.318, the yield of adamantane was reduced to 23.4%. This demonstrates that an excess amount of co-catalyst may disadvantageously affect the activity of the acidic ionic liquid so that the yield of adamantane cannot be increased significantly.

Furthermore, in Examples 1 and 13, the same amount of deionized water and the same amount of the same acidic ionic liquid were used. When isomerization was conducted at 70° C. as shown in Example 1, the isomerization conversion of THDCPD was 24.2%, the selectivity of adamantane was 72.2%, and the yield of adamantane was 17.5%. On the other hand, when isomerization was conducted at 90° C. as shown in Example 13, the isomerization conversion of THDCPD was 40.8%, the selectivity of adamantane was 78.2%, and the yield of adamantane was 31.9%, which are significant increases as compared to those in Example 1.

As shown in Examples 11 and 14, in which isomerization was conducted at the same temperature using the same acidic ionic liquid and the same amount of the same co-catalyst, when the molar ratio of $AlCl_3$ in the acidic ionic liquid was increased from 0.65 (Example 11) to 0.75 (Example 14), the isomerization conversion of THDCPD was increased from 34.1% to 55.7%, the selectivity of adamantane was increased from 70.4% to 79.1%, and the yield of adamantane was increased from 24.0% to 44.1%.

In Examples 15-17, BMIC, BMIB, or TEAC was used for preparing the acidic ionic liquid. Although the selectivity of adamantane was reduced in Examples 15 and 16 in which BMIC or BMIB was used, the isomerization conversion of THDCPD was increased due to the addition of the co-catalyst, and thus the yield of adamantane was increased.

In sum, the catalytic activity of the acidic ionic liquid can be increased by adding the co-catalyst selected from water, alcohol, acid, ester, hydrogen peroxide, hydrogen chloride, or combinations thereof to increase the isomerization conversion of THDCPD and thus the yield of adamantane significantly.

While the present invention has been described in connection with what are considered the most practical embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for producing adamantane, comprising the steps of:
    preparing a catalytic composition including an acidic ionic liquid and a co-catalyst, wherein the acidic ionic liquid includes aluminum chloride and a quaternary onium compound selected from the group consisting of a quaternary ammonium halide, a quaternary phosphonium halide, and a combination thereof, and wherein the co-catalyst is selected from the group consisting of water and an aqueous solution of 1-50 wt. % hydrogen peroxide; and
    subjecting a tetrahydrodicyclopentadiene-containing component to isomerization in the presence of the catalytic composition to form adamantane.

2. The method according to claim 1, wherein the tetrahydrodicyclopentadiene-containing component includes a tetrahydrodicyclopentadiene compound selected from the group consisting of exo-tetrahydrodicyclopentadiene, endo-tetrahydrodicyclopentadiene, and a combination thereof.

3. The method according to claim 1, wherein the quaternary ammonium halide is selected from the group consisting of ammonium halide, pyridinium halide, imidazolium halide, pyrrolium halide, pyridinium halide, pyrimidinium halide, pyrazinium halide, pyridazinium halide, alkyl-substituted ammonium halide, alkyl-substituted pyridinium halide, alkyl-substituted imidazolium halide, alkyl-substituted pyrrolium halide, alkyl-substituted pyrimidinium halide, alkyl-substituted pyrazinium halide, alkyl-substituted pyridazinium halide, and combinations thereof.

4. The method according to claim 3, wherein each of said alkyl-substituted ammonium halide, said alkyl-substituted pyridinium halide, said alkyl-substituted imidazolium halide, said alkyl-substituted pyrrolium halide, said alkyl-substituted pyrimidinium halide, said alkyl-substituted pyrazinium halide, and said alkyl-substituted pyridazinium halide contains an alkyl substituent having a carbon number ranging from 1 to 18.

5. The method according to claim 1, wherein the quaternary phosphonium halide is tetraalkylphosphonium halide.

6. The method according to claim 1, wherein a molar ratio of aluminum chloride to the acidic ionic liquid ranges from 0.5 to 0.9.

7. The method according to claim 2, wherein the tetrahydrocyciopeniadiene compound is endo-tetrahydrodicyclopentadiene, the tetrahydrodicyclopentadiene-containing component further including a solvent for dissolving endo-tetrahydrodicyclopentadiene, the solvent included in the tetrahydrodicyclopentadiene-containing component being used in an amount greater than 0 wt % and up to 50 wt % based on 100 wt % of the tetrahydrodicyclopentadiene-containing component.

8. The method according to claim 7, wherein the solvent included in the tetrahydrodicyclopentadiene-containing component is selected from the group consisting of a $C_5$-$C_{18}$ n-alkane, a $C_5$-$C_{18}$ iso-alkane, a $C_5$-$C_{18}$ neo-alkane, a $C_5$-$C_{18}$ cycloalkane, a $C_1$-$C_6$ halogen-containing hydrocarbon, and combinations thereof.

9. The method according to claim 1, wherein the isomerization is conducted at a temperature ranging from 25 to 150° C.

\* \* \* \* \*